United States Patent
Beyer et al.

(10) Patent No.: US 10,524,650 B2
(45) Date of Patent: Jan. 7, 2020

(54) SCANABLE TRAY FOR PRODUCING A DENTAL PROSTHESIS

(71) Applicant: HERAEUS KULZER GMBH, Hanau (DE)

(72) Inventors: Mario Beyer, Bad Homburg (DE); Norbert Ueberück, Maintal (DE); Uwe Böhm, Hanau (DE)

(73) Assignee: KULZER GMBH, Hanau (DE)

( * ) Notice: Subject to any disclaimer, the term of this patent is extended or adjusted under 35 U.S.C. 154(b) by 0 days.

(21) Appl. No.: 14/897,768

(22) PCT Filed: Jun. 13, 2014

(86) PCT No.: PCT/EP2014/062331
§ 371 (c)(1),
(2) Date: Dec. 11, 2015

(87) PCT Pub. No.: WO2014/198873
PCT Pub. Date: Dec. 18, 2014

(65) Prior Publication Data
US 2016/0143716 A1    May 26, 2016

(30) Foreign Application Priority Data
Jun. 14, 2013   (DE) .......... 10 2013 211 200

(51) Int. Cl.
*A61B 1/24*    (2006.01)
*A61C 9/00*    (2006.01)
(Continued)

(52) U.S. Cl.
CPC ............. *A61B 1/24* (2013.01); *A61B 5/0088* (2013.01); *A61C 9/0006* (2013.01); *A61C 13/0019* (2013.01); *A61B 2090/3912* (2016.02)

(58) Field of Classification Search
CPC ............ A61C 13/0004; A61C 13/0019; A61C 9/0006; A61C 9/004; A61C 9/0046;
(Continued)

(56) References Cited

U.S. PATENT DOCUMENTS

| 4,016,650 A | 4/1977 | Leusner et al. |
| 5,188,529 A * | 2/1993 | Luth ............... A61C 19/05 |
| | | 433/68 |

(Continued)

FOREIGN PATENT DOCUMENTS

| CN | 201 414 849 Y | 3/2010 |
| DE | 2 454 216 A1 | 5/1976 |

(Continued)

OTHER PUBLICATIONS

International Search Report dated Aug. 21, 2014, dated Nov. 19, 2014.

*Primary Examiner* — Wade Miles
*Assistant Examiner* — Matthew P Saunders
(74) *Attorney, Agent, or Firm* — Norris McLaughlin, P.A.

(57) ABSTRACT

A method for taking an impression for producing a dental prosthesis involves:
A) generating an impression of regions of the upper jaw and lower jaw of a patient using an at least two-part tray, whereby the tray is inserted into the oral cavity of the patient;
B) fixing the at least two tray parts to each other or against each other;
C) determining the position and orientation of the at least two tray parts with respect to each other; and
D) taking the tray parts out of the oral cavity of the patient. Also disclosed is the tray for implementing the method, whereby at least one marking is arranged on the surface of each tray part, and a device for intra-oral determination of the orientation and position of the (Continued)

marking and, thus, the at least two tray parts, is provided, whereby the device comprises a computer and a recording facility.

9 Claims, 4 Drawing Sheets

(51) Int. Cl.
*A61B 5/00* (2006.01)
*A61C 13/00* (2006.01)
*A61B 90/00* (2016.01)

(58) Field of Classification Search
CPC ........... A61C 9/0053; A61C 9/00; A61B 1/24; A61B 5/0088; A61B 2090/3912
USPC .......... 433/6, 24, 37, 41–48, 72–73, 75, 213
See application file for complete search history.

(56) References Cited

U.S. PATENT DOCUMENTS

| | | | | |
|---|---|---|---|---|
| 5,427,117 A * | 6/1995 | Thornton | ................ | A61F 5/566 128/848 |
| 5,722,828 A * | 3/1998 | Halstrom | ............. | A61C 19/045 433/69 |
| 5,823,778 A * | 10/1998 | Schmitt | .................... | A61C 9/00 433/214 |
| 6,213,769 B1 * | 4/2001 | Bettega | .................. | A61C 19/04 433/56 |
| 7,530,355 B2 * | 5/2009 | Berghash | ............. | A63B 71/085 128/857 |
| 7,899,221 B2 * | 3/2011 | Weber | ................ | A61C 13/0004 382/128 |
| 8,312,884 B2 * | 11/2012 | Fuselier | .................. | A61F 5/566 128/846 |
| 8,316,857 B2 * | 11/2012 | Thornton | ................ | A61F 5/566 128/846 |
| 8,316,858 B2 * | 11/2012 | Thornton | .................. | A61F 5/56 128/846 |
| 8,376,742 B2 * | 2/2013 | Kushner | .................. | A61C 5/00 433/37 |
| 8,544,472 B2 * | 10/2013 | Gaskell | ................ | A61C 17/043 128/202.27 |
| 8,821,158 B1 * | 9/2014 | Hultgren | ...................... | 433/215 |
| 2003/0204150 A1 * | 10/2003 | Brunner | ................ | A61B 5/1114 600/590 |
| 2004/0032594 A1 * | 2/2004 | Weber | ................ | A61C 13/0004 356/601 |
| 2005/0084817 A1 * | 4/2005 | Teng | ..................... | A61C 19/045 433/68 |
| 2006/0154198 A1 * | 7/2006 | Durbin | ..................... | A61C 9/00 433/29 |
| 2006/0275736 A1 * | 12/2006 | Wen | ......................... | A61C 9/00 433/213 |
| 2007/0231774 A1 * | 10/2007 | Massad | ................... | A61C 19/05 433/213 |
| 2010/0035210 A1 | 2/2010 | Suchan et al. | | |
| 2010/0099056 A1 * | 4/2010 | Millstein | ............... | A61C 9/0053 433/71 |
| 2010/0106275 A1 * | 4/2010 | Andersson | ........... | A61C 9/0006 700/98 |
| 2010/0239136 A1 * | 9/2010 | Gandyra | ................ | G01B 11/03 382/128 |
| 2010/0297572 A1 * | 11/2010 | Kim | ...................... | A61C 9/0006 433/71 |
| 2011/0195373 A1 * | 8/2011 | Waugh | ...................... | A61C 7/02 433/24 |
| 2011/0232652 A1 * | 9/2011 | Levendowski | .......... | A61F 5/566 128/848 |
| 2011/0290005 A1 * | 12/2011 | Hart | .................... | G01B 11/0658 73/37.9 |
| 2012/0064477 A1 * | 3/2012 | Schmitt | ................. | A61C 9/0006 433/29 |
| 2012/0237892 A1 * | 9/2012 | Lang | ......................... | A61C 19/05 433/73 |
| 2013/0130195 A1 * | 5/2013 | Evenson | .............. | A61C 19/052 433/68 |
| 2013/0203009 A1 * | 8/2013 | Mutsafi | ................. | A61C 8/0001 433/27 |
| 2013/0280671 A1 * | 10/2013 | Brawn | ................. | A61N 5/0603 433/24 |
| 2013/0280672 A1 * | 10/2013 | Thompson | ........... | A61C 9/0006 433/42 |
| 2014/0170583 A1 * | 6/2014 | Kuo | .......................... | A61B 1/24 433/3 |

FOREIGN PATENT DOCUMENTS

| | | |
|---|---|---|
| DE | 20 2005 004 923 U1 | 7/2006 |
| DE | 10 2010 049 159 A1 | 4/2012 |
| DE | 10 2010 049 266 A1 | 4/2012 |
| FR | 2 964 854 A1 | 3/2012 |

* cited by examiner

SCANABLE TRAY FOR PRODUCING A DENTAL PROSTHESIS

This application is a 371 of International Patent Application No. PCT/EP2014/062331, filed Jun. 13, 2014, which claims priority of German Patent Application No. 10 2013 211 200.9, filed Jun. 14, 2013, the contents of both patent applications being incorporated herein by reference.

The invention relates to a method for taking an impression of at least partial regions of the upper and lower jaw for producing a dental prosthesis, in particular a denture, and a tray for taking an impression of at least partial regions of the upper and lower jaw of a patient for implementing said method, as well as a device for intra-oral determination of the orientation and position of at least two tray parts with respect to each other for taking an impression of at least partial regions of the upper and lower jaw of a patient with respect to each other.

Dental prostheses and dentures are used to replace missing teeth. Dentures can be used to manage whole rows of missing teeth or a fully toothless jaw. In a fully digital work-flow for producing a partial dental prosthesis or full prosthesis by means of a scanner or other imaging method, the relationship and the range of motion of the toothless or partially toothed jaws with respect to each other need to be recorded, digitised, and then processed further. Digital methods for recording the situation in the oral cavity of a patient are known, for example, from US 2010 035 210 A1, DE 10 2010 049 266 A1, DE 10 2010 049 159 A1, and CN 201 414 849 Y. In these methods, an impression of the at least partially toothless jaw is taken, digitised, and the data thus obtained is used to generate a dental prosthesis with a CAD/CAM method.

A, usually two-part, tray (one tray part for the upper jaw and one tray part for the lower jaw) is inserted into the oral cavity of the patient, whereby the tray is being filled with a pasty impression material, which is then pressed onto the upper jaw and lower jaw of the patient to be treated. A tray should be understood as being an impression tray. In particular in a toothless jaw or largely toothless jaw to be managed with dentures, it is necessary for the subsequent configuration of teeth in the denture and/or dental prosthesis to know, which means to determine, the distance and the mobility of the lower jaw from and with respect to the upper jaw, in particular of the at least partially toothed or toothless alveolar ridge of the lower jaw and/or upper jaw, such that the dental prosthesis is suitable for mastication and also satisfies the existing aesthetic requirements.

Currently, this is being attained in that the two tray parts are fixed to each other in a suitable central position of the jaw, which corresponds to that of the closed mouth of the patient. For this purpose, the tray parts can be connected and fixed to each other by means of a curing foam or an impression material. Subsequently, the tray parts affixed to each other are taken out of the oral cavity and the impression and the orientation and position of the tray parts with respect to each other are used to produce the dental prosthesis. Subsequently, the impressions of the upper jaw and lower jaw are used to produce the dental prosthesis.

This is associated with a disadvantage in that the tray parts affixed to each other are relatively large as compared to the oral cavity of the patient such that the patient often experiences the removal as unpleasant. Moreover, the impressions may be impacted adversely when the large tray is taken out, which might lead to a deterioration of the dental prosthesis produced by means of the impression, or the impression-taking may need to be repeated.

Accordingly, it is the object of the invention to overcome the disadvantages of the prior art. Specifically, a method is to be devised that is less error-prone and less unpleasant for the patient. Concurrently, the method should be inexpensive and easy to implement, such that it can be used in a standard dental office as well.

The objects of the invention are solved by a method for producing a dental prosthesis, in particular a denture, comprising the procedural steps of:

A) generating an impression of at least partial regions of the upper jaw and lower jaw of a patient, preferably an impression of the lower and/or upper alveolar ridge, using an at least two-part tray in the oral cavity of the patient, whereby the tray is being inserted into the oral cavity of the patient for this purpose;

B) fixing the at least two tray parts to each other or against each other in the oral cavity of the patient;

C) followed by determining the position and orientation of the at least two tray parts with respect to each other in the oral cavity of the patient; and D) followed by taking the tray parts out of the oral cavity of the patient.

The fixing of the tray parts can be effected, in case of a two-part tray, with a lockable screw, a spring-loaded bearing device registration, an elastic bearing device registration or a similar facility by exerting a force on the tray parts by the patient biting on it. If no corresponding locking mechanism or other attachment option is present, the patient may need to keep biting with force.

A tray according to the invention is at least two-part and comprises at least one tray part for the upper jaw and at least one tray part for the lower jaw. However, the tray parts for the upper jaw and lower jaw can just as well be subdivided into further tray parts in order to provide an even more variable tray, which can be adapted to regions of the anatomy of the respective jaw of the patient.

The invention can preferably provide for an impression material to be filled into the tray to generate the one impression of at least partial regions of the upper and lower jaw, in particular the dentition impression preceding step A). The impression is important for determining the underside of the dental prosthesis, preferably for generating an impression of at least partial regions of the upper and lower jaw, in particular of the denture. According to one embodiment of the invention the impression is important for determining at least parts of the edentulous mouth or at least one single tooth to the whole dentition.

A refinement of the method according to the invention can provide for the position and orientation of the tray parts with respect to each other to be determined by means of an imaging method.

Images of this type can be recorded, for example and preferably according to the invention, with an intra-oral scanner or an intra-oral camera. Imaging methods are being employed in dentistry and dental engineering ever more anyway such that the method then does not involve additional expenses related to an additional apparatus. According to the invention, it is preferred to use imaging methods working with light in the visible range, preferably between 390 nm and 630 nm.

Moreover, the invention can provide that the position and orientation of the tray parts with respect to each other are determined by means of at least one marking on each of the tray parts, whereby it is preferable to determine the position and orientation of the markings with respect to each other and to use the data thus obtained to determine the position and orientation of the tray parts with respect to each other.

The markings can simply be painted patterns, which can preferably be arranged on the buccal or labial surface of the tray. It is feasible just as well to use different-coloured patterns, provided a colour scanner is used or if colour images are recorded. It is preferable to use three-dimensional contoured markings, which allow any tilting of the marking to be easily recognisable and to be measured. It is important in this context that the markings are not so symmetrical that a rotation of the tray part about any axis cannot be recognised by means of a rotation of the marking.

Moreover, the invention preferably proposes, for determination of the position and orientation of the tray parts with respect to each other, that regions of the tray parts, preferably comprising the markings, are recorded, digitised, and analysed in computer-based manner by means of a stereo image or at least two images taken from different perspectives.

Using this method, especially three-dimensional markings can be analysed and recognised particularly well and easily.

A preferred refinement of the invention can provide, for determination of the position and orientation of the tray parts with respect to each other, that the surfaces of the tray parts, at least regions thereof, are imaged intra-orally or scanned with an optical method, whereby it is preferable to image or scan at least two markings of at least two different tray parts concurrently.

This can preclude motion of the jaw and thus a change of the position and orientation of the markings with respect to each other between the images.

Moreover, the invention proposes to detach the fixation of at least two tray parts with respect to each other or on each other before removal from the oral cavity of the patient and after the determination of the position and orientation of the at least two tray parts with respect to each other, and to take the tray parts out of the oral cavity separately.

This is advantageous in that smaller tray parts, rather than the entire tray, can be taken out of the oral cavity of the patient. Firstly, this is more gentle for the patient and, secondly, it prevents the impressions taken out in this manner to be affected adversely.

According to a preferred refinement, the invention can just as well provide that a lip shield is used as at least a third tray part and is preferably attached to the tray part for the upper jaw, whereby the lip shield preferably has at least one marking arranged on it that is used to determine the position and orientation of the lip shield with respect to the tray part for the upper jaw and/or that the lip shield has a surface provided on it on which can be written and which serves to have aesthetic features drawn on it and which has at least one aesthetic feature drawn on it.

The lip shield keeps the lip distant from the impression and can also be used concurrently with a method according to the invention to determine the position and orientation of the tray parts with respect to each other and also for marking further aesthetic features. It is particularly preferable to read-out such markings in a computer-based manner. It is preferable not to separate the lip shield from the other tray parts and not to take it out separately.

A refinement of the invention proposes that the position and orientation of the at least two tray parts with respect to each other is stored and used in a computer to calculate a virtual model of the dental prosthesis to be produced, preferably is stored and used to calculate the orientation and size of the dental prostheses of a denture for the upper jaw and/or a denture for the lower jaw of the patient.

This step effects further automation and simplification of the production of the dental prostheses and/or dentures.

In this context, the invention can provide the dental prosthesis to be produced by means of a CAD/CAM or rapid prototyping method, whereby the position and orientation of the at least two tray parts with respect to each other are utilised in the generation of a virtual CAD model.

The method according to the invention can be implemented particularly efficiently through the present embodiment, as well as the following embodiment.

The invention can just as well provide that an impression of the upper jaw and/or lower jaw of the patient, preferably of the at least partially toothed or toothless (edentulous) upper and/or lower alveolar ridge, taken with the tray is used to generate a data set by reading the three-dimensional surface structure of the impression of the upper jaw and/or lower jaw of the patient, preferably of the at least partially toothed or toothless (edentulous) upper and/or lower alveolar ridge, and that the data set is preferably used to generate the virtual CAD model of the dental prosthesis, in particular of the denture, which is used to produce the real dental prosthesis, in particular the real denture.

According to a refinement according to the invention, the invention can provide a rigid connecting element with multiple markings, in particular an irregular raster or an irregular grid, to be attached to the at least two tray parts and the connecting element to be used to determine the position and orientation of the at least two tray parts with respect to each other.

This enables the implementation of the method even if the tray parts are distant from each other, without having to use large-scale recording methods.

The objects of the invention are also solved by a tray for taking an impression of at least partial regions of the upper and lower jaw of a patient for implementing a method of this type, comprising at least two tray parts, whereby at least one marking is arranged on the surface of each tray part and enables the determination of the position and orientation of the markings and tray parts with respect to each other.

In this context, the invention can provide the markings to be contoured elements arranged on the surface of the tray parts, whereby the geometry of the contoured elements allows the position and orientation of the contoured elements with respect to each other to be determined.

The contoured elements are particularly well-suited in stereo-images for recognition of the position and orientation of the markings, and thus of the tray parts, with respect to each other.

The invention can just as well provide the markings to be arranged on the edge of the tray parts such that the markings of adjacent tray parts that are inserted into the oral cavity of the patient are situated as close to each other as possible, and preferably the markings can be imaged on just one image of a recording device in the oral cavity of the patient.

What this attains is that the markings are as close to each other as possible in the inserted state of the tray in the oral cavity and that a small-sized recording or a small section of the surface of the tray parts is sufficient for determination of the position and orientation of the tray parts with respect to each other.

A refinement of the invention proposes to provide at least one tray part for the upper jaw, in particular for the toothless upper alveolar ridge, and at least one tray part for the lower jaw, in particular for the toothless lower alveolar ridge, whereby the tray parts can be placed at a distance from each other by means of a screw or a pin, preferably can be attached at an adjustable distance from each other.

In this context, the invention can provide the pin to comprise a mobile pestle that is supported against the tray part as in a bearing in spring-loaded manner. Preferably, the invention can provide the screw to be lockable.

Also, regarding said trays that can be situated at a distance, the invention can provide the pin or screw to be arranged on one of the tray parts, whereby the other tray part comprises a recess for accommodation of the tip of the screw or tip of the pin, in particular for accommodation of the pestle. In this context, the invention can preferably provide the recess to comprise a matching counter-thread for the screw or the recess to be a negative fit for the tip of the pin, in particular of the pestle, whereby the tip of the pestle preferably is arranged appropriately mobile in the recess such that it can be inclined towards all sides.

The use of a pin enables the tray parts to be situated at a defined distance from each other. The elastic, in particular pneumatic, most preferred spring-loading attains comfortable and bite force-based distancing of the tray parts. Due to the ability of the tip of the pestle to be inclined, the tray parts can still move with respect to each other. In this case, the support of the tip of the pestle serves as a ball joint for connecting the two tray parts.

The invention can just as well provide the tray parts to comprise a matte, in particular an essentially nonreflecting surface, and preferably also a light-coloured, surface at least in the region of the marking, preferably a rough surface which, in particular, comprises a mean roughness between 0.5 µm and 10 µm.

A tray surface of this type supports the utility of imaging methods, since reflections and other interfering optical effects can thus be prevented.

The objects of the invention are also solved by a device for intra-oral determination of the orientation and position of at least two tray parts for taking an impression of at least partial regions of the upper and lower jaw of a patient with respect to each other, preferably of an impression of the at least partially toothed or toothless upper and/or lower alveolar ridge, whereby the device is suitable for implementing a method according to the invention and the device comprises a computer and a recording facility, in particular an intra-oral scanner or an intra-oral camera, that can be used to determine the position and orientation of the tray parts with respect to each other by means of an imaging method and a computer-based analysis of the images for a known shape of the tray parts, whereby said tray preferably is a separate part of the device and the position and orientation of the tray parts with respect to each other can be determined by means of a computer-based analysis of the images of the known markings on the tray parts.

In this context, the invention can provide the device to comprise a 3D printer for producing a dental prosthesis, in particular a denture, and to be connected to the computer for producing the dental prosthesis, in particular the denture, whereby the computer is programmed appropriately such that the position and orientation of the tray parts with respect to each other has a significant influence on the build-up of the dental prosthesis, in particular of the denture, preferably on the configuration of teeth in the dental prosthesis.

The invention is based on the surprising insight that determining the position and orientation of the tray parts with respect to each other in the oral cavity of the patient allows the tray parts to be disconnected before taking them out of the oral cavity of the patient. As a result, the tray parts are then smaller and can be removed more comfortably for the patient and any adverse influence on the impressions generated with the trays can be prevented. The marking on the tray parts enables accurate determination of the position and orientation of the tray parts with respect to each other, since the position and orientation of the markings on the surface of the tray parts is known. In a subsequent digitisation of the impression, preferably of an impression of at least partial regions of the upper and lower jaw, in which the position and orientation of the impression material with respect to the tray part is determined as well, the desired position and orientation of the contact surfaces of the dental prostheses with respect to each other in the oral cavity of the patient can be determined and thus a suitable tooth configuration in the prosthesis can be determined and/or calculated. In particular at least the static occlusion and if at least two, in particular multiple positions, mor preferred 2 to 30 positions, 3 to 10 correlated positions, of the trays will be determined the dental occlusion/ dental articulation can be determined according to the method and trays of the invention. The dental prosthesis produced from the data and/or the denture thus produced has the desired properties with regard to biting and mastication and also satisfies the aesthetic requirements without the position and orientation of the tray parts and/or impressions with respect to each other having to be determined outside the oral cavity of the patient.

BRIEF DESCRIPTION OF THE DRAWINGS

Exemplary embodiments of the invention shall be illustrated in the following on the basis of three schematic figures, though without limiting the scope of the invention. In the figures.

Figure 1:
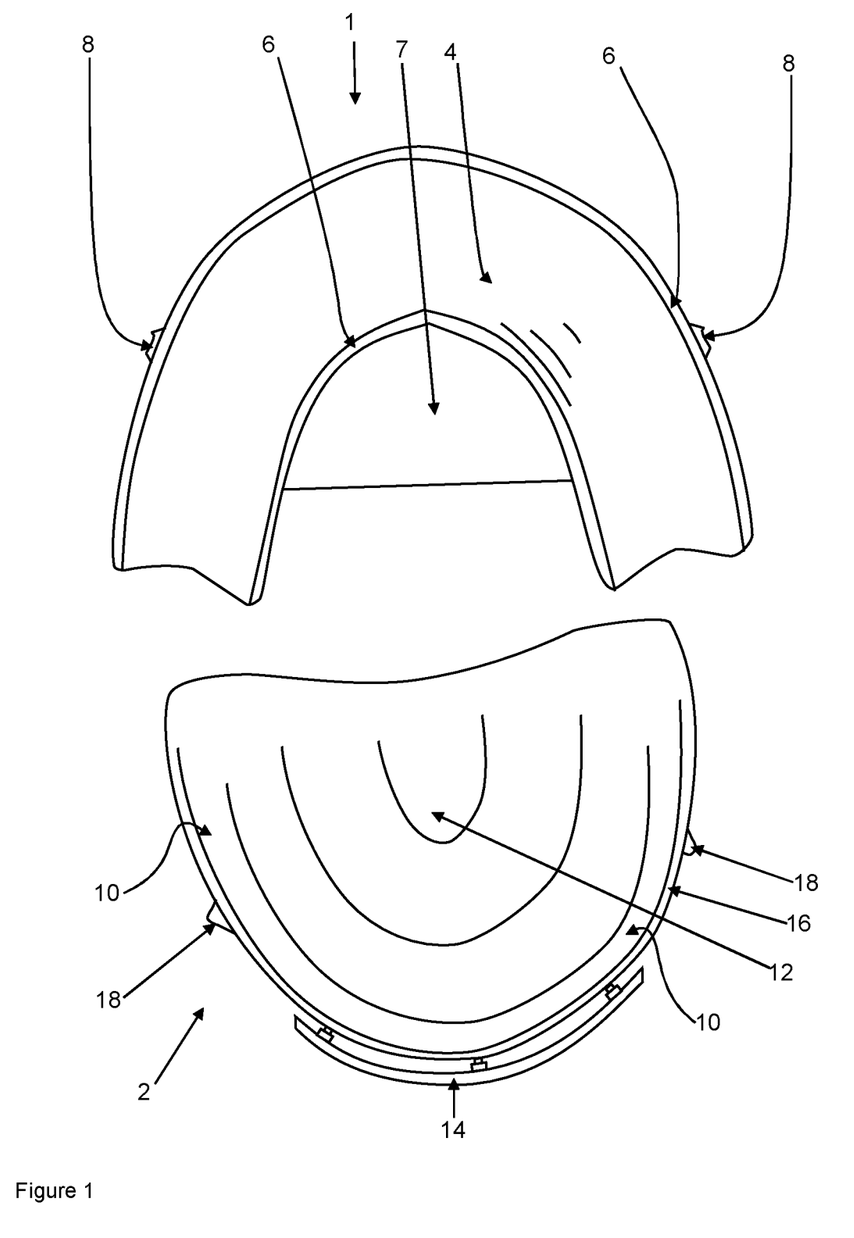
FIG. 1: shows a schematic perspective top view onto two tray parts of a tray according to the invention for dental impressions.

FIG. 1 shows a schematic perspective view of a tray according to the invention for dental impressions. The tray is subdivided into two tray parts 1, 2. The first tray part 1 is intended for the lower jaw, the second tray part 2 is intended for the upper jaw. The tray parts 1, 2 are intended to have an impression material (not shown) filled into them, which is then to be pressed against the alveolar ridges of the patient resulting in a negative image of the oral cavity situation of the patient being present in the impression material. Methods of this type are known and can be looked up in the prior art.

For this purpose, the tray part 1 for the lower jaw comprises a bed 4 for accommodation of the impression material, which is shaped alike the dental arch and is designed to be sufficiently large to surround lower jaw dental arches of various shapes. The bed 4 is bounded on both sides by walls 6 that extend out of the image plane in FIG. 1 and towards the observer. The bed 4 thus forms a U-shaped contour that surrounds the dental arch of the lower jaw in the way of a U-shaped profile. The curvature of the bed 4 is indicated by three short lines in the drawing of tray part 1 for the lower jaw in FIG. 1.

A tongue shield 7 is arranged in the direction into the image plane and is to keep away the tongue of the patient. Markings 8 in the form of a non-symmetrical contour are arranged on the side surfaces of the outer (buccal) wall.

Analogous to bed 4 of tray part 1 for the lower jaw, the tray part 2 for the upper jaw also has a bed 10 for accommodation of an impression material (not shown) that is lowered into the image plane in FIG. 1, as is indicated through the three long lines in FIG. 1. The tray part 2 for the upper jaw comprises in its centre a palate plate 12, which, in its inserted state, faces in the direction of the palate of the patient and is well-suited for pressing the impression material against the desired regions of the oral cavity. From there, the tray part 2 for the upper jaw drops off in the direction of the bed 10. The bed 10 is bounded by a wall 16 that extends upwards out of the image plane according to FIG. 1 such that the bed 10 forms a U-shaped groove for accommodation of the dental arch of the upper jaw of the patient.

The labial (lip-side) outside of the wall 16 has a lip shield 14 attached to it at three adjustable brackets. The purpose of the lip shield 14 is to keep the lip of the patient at a distance from the tray while taking the impression. The buccal (cheek-side) outsides of the wall 16 have two markings 18 in the form of three-dimensional contours arranged on them.

The markings 8, 18 of the tray parts 1, 2 are situated approximately one over the other when the tray is inserted in the mouth. The tray parts 1, 2 can be affixed to each other by means of connecting means, which are arranged on the side of the tray parts 1, 2 away from the image and are thus not visible in FIG. 1.

Figure 2:
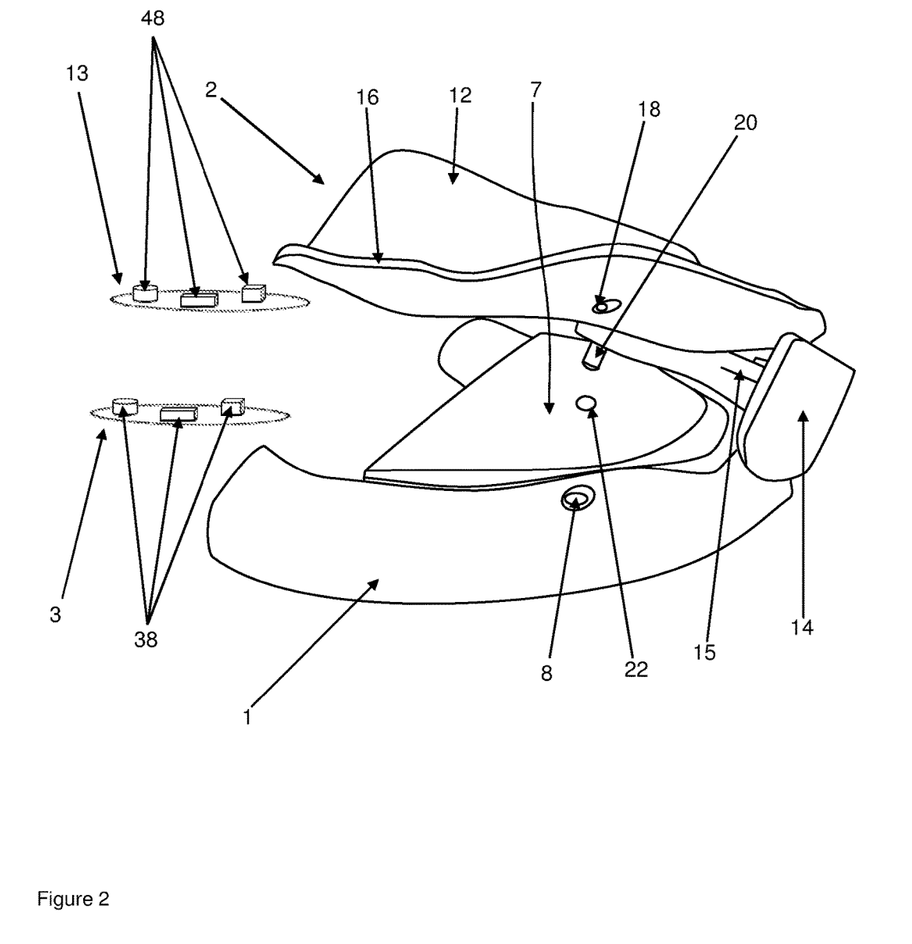
FIG. 2: shows a schematic perspective side view of the tray according to the invention for dental impressions.

FIG. 2 shows a schematic perspective view of the tray according to the invention for dental impressions according to FIG. 1. Here, the tray part 1 for the lower jaw is arranged below the tray part 2 for the upper jaw. The arrangement of the tray parts 1, 2 in FIG. 2 closely corresponds to the assembled state that is being built-up in the oral cavity of the patient. For this purpose, a spring-loaded bearing device registration 20 or a screw 20, which is arranged on the underside of the palate plate 12, is supported on a recess 22 and/or screwed into the recess 22. The recess 22 is a recess in the upper side of the tongue shield 7, whereby the recess has a surface that corresponds to the negative image of the tip of the bearing device registration 20. Alternatively, the recess 22 is a hole comprising a counter-thread for the screw 20. As a result, the tray parts 1, 2 can be connected to each other by means of the bearing device registration 20 and/or the screw 20 and the recess 22. For a more stable connection, a detachable locking mechanism can be provided that connects the bearing device registration 20 and/or the screw 20 to the recess 22. Preferably, the bearing device registration 20 is supported in the recess 22 as in a bearing such that it can be inclined in all directions in the way of a ball joint.

The lip shield 14 is connected to a bracketing 15 on the front side of the tray part 2 for the upper jaw. The length of the lip shield bracketing 15, and thus the distance between the lip shield 14 and the second tray part 2, can be adjusted. Likewise, the length of the bearing device registration 20 can be adjusted, i.e. that the length by which the bearing device registration 20 projects beyond the surface of the underside of the palate plate 12 can be adjusted. Moreover, the bearing device registration 20 is supported as in a bearing in spring-loaded manner such that the tray parts 1, 2, when inserted in the patient, can be pushed more closely together by the patient biting on them. For the same purpose, the screw 20 can be lockable (for example by means of a bolt or lock nut). Alternatively, the screw 20 can just as well be very difficult to rotate in the counter-thread of the hole such that there is no need for a locking mechanism. The screw 20 can also be supported as in a bearing in spring-loaded manner.

The markings 8, 18 are visible on the surface of the tray parts 1, 2 and are situated approximately one above the other in the assembled state of the tray. The markings 8, 18 are unsymmetrical, elevated contours on the buccal surface of the tray parts 1, 2. One or more additional markings can also be arranged on the lip shield 14 just as well. The markings 8, 18 serve for recognition of the position and orientation of the tray parts 1, 2 with respect to each other. If the position and orientation of the tray parts 1, 2 is known, the impressions and their position and orientation can be used to accurately determine the oral cavity situation, as is illustrated briefly in the following based on an exemplary embodiment according to the invention of a method according to the invention.

Firstly, an impression material (not shown) is filled into the beds 4, 10 of the tray parts 1, 2. The tray parts 1, 2 are introduced separately into the oral cavity of a patient and are pressed onto the toothless or partially toothless dental arch. Motions of the jaw of the patient are used in known manner to determine the desired ideal position of the tray parts 1, 2 with respect to each other. The spring-loaded bearing device registration 20 or the adjustable screw 20 generate a resistance that is variable and can be felt by the patient and leads to a good impression result. After taking an impression in known manner and while the tray parts 1, 2 are still situated in the oral cavity of the patient, the tray parts 1, 2 can be fixed to each other or the position is maintained by the biting force of the patient. A scanner (for example an intra-oral scanner) or any other imaging method is then used to image the buccal outside surfaces of the tray parts 1, 2. Both markings 8, 18 can be recognised on a stereoscopic image or two images recorded from different and known perspectives and thus allow the position and orientation of the tray parts 1, 2 with respect to each other to be determined. If the two markings 8, 18 are not sufficiently close to each other, rigid connecting element 3, 13 having additional markings 38, 48 in the form of a grid or any other defined pattern can be placed on or can be attached to the surface of the tray parts 1, 2. If the position and orientation of the first marking 8 and second marking 18 can be related to the additional markings 38, 48, for example the grid pattern, the position and orientation of the markings 8, 18 with respect to each other can be determined via the relative position and orientation of the additional markings 38, 48.

The data thus obtained are processed in computer-based manner and are used as the basis for the CAD model of the dental prosthesis and/or denture generated using said digitised impression. The data thus obtained are important, in particular, for the set-up of artificial teeth of the proper size and alignment in the dental prosthesis and/or denture.

Once the position and orientation of the tray parts 1, 2, in particular the intraoral position and orientation, with respect to each other are determined by intra-oral technique, the tray parts 1, 2 can be separated from each other again and can be taken out of the oral cavity of the patient separately. As a result, the patient does not have to open the mouth as much as when tray parts 1, 2 fixed to each other as an entire tray need to be taken out of the oral cavity of the patient. Aside from the patient comfort, this is advantageous in that the impressions in the impression material are exposed to less mechanical stress and in that the probability of undesired shape change of the impressions is thus reduced.

It may be feasible to write on the labial outside of the lip shield 14 in order to mark aesthetic features such as the smile line, width of the nose, resting position or other information on the lip shield 14. Said markings on the lip shield 14 can also be read and digitised and can contribute to the CAD model and thus have an influence on the shape of the dental prosthesis and/or denture thus produced.

Figure 3A:
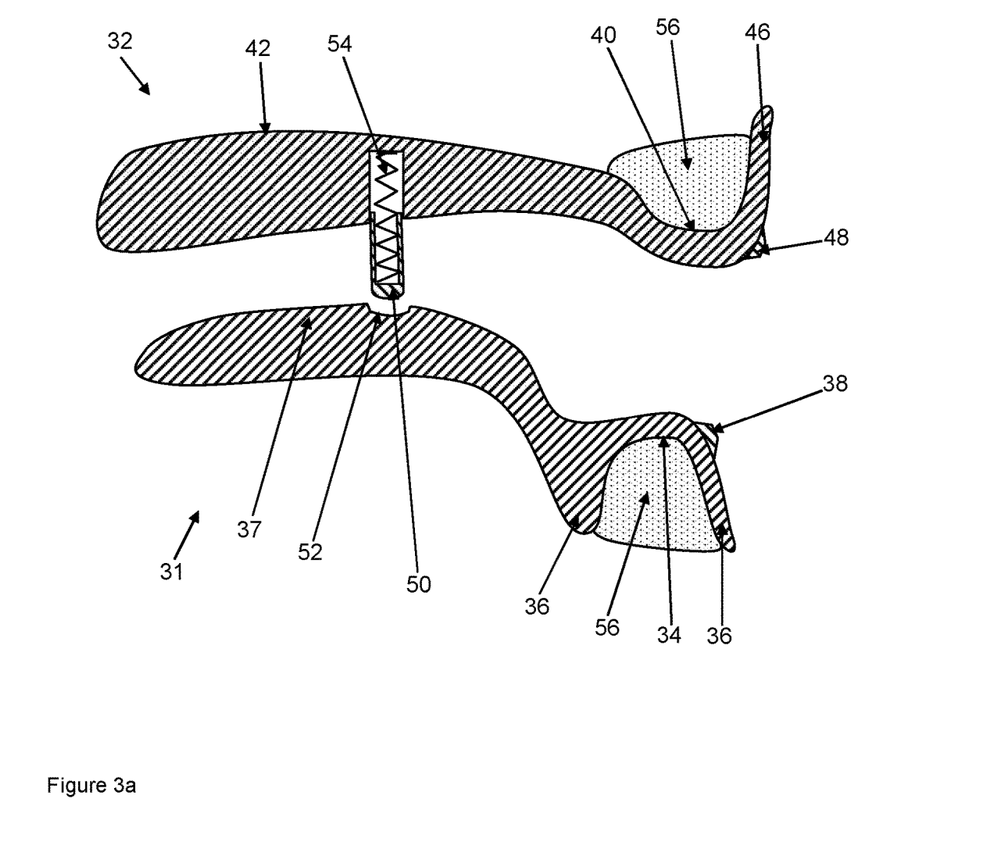
FIGS. 3a, 3b: show a schematic cross-sectional view of an alternative tray according to the invention for dental impressions.

FIG. 3a shows a schematic cross-sectional view of another tray according to the invention for dental impressions with a similar basic structure as the tray according to FIGS. 1 and 2, whereby the present embodiment does not comprise a lip shield. The tray has a first tray part 31 for the lower jaw and a second tray part 32 for the upper jaw. A U-shaped bed 34 of the first tray part 31 has walls 36 for its boundaries. A tongue shield 37 is provided in the middle of the first tray part 31.

A marking 38 is arranged on the labial outside of the outer wall 36 and serves for determining the position and orientation of the first tray part 31.

The second tray part 32 comprises a bed 40 for accommodation of the dental arch of the upper jaw, and a palate plate 42. The bed 40 has a wall 46 for its boundary on its labial outside. A marking 48 is arranged on the labial outside of the wall and faces in the direction of the first part 31. A cylindrical bearing device registration 50 is arranged, such as to be mobile, in a hole in the palate plate 42. Suitable measures, such as for example a projection or locking mechanism, can be used to protect the bearing device registration 50 from falling out. The spring-loaded bearing device registration 50 determines the distance between the tray parts 31, 32.

The upper side of the tongue shield 37 of the first tray part 31 has a recess 52 for accommodation of the tip of the spring-loaded bearing device registration 50 arranged in it. By means of a spring 54, the bearing device registration 50 is supported against the palate plate 42 as in a bearing such as to be mobile. The walls of the bearing device registration 50 can be designed to be somewhat elastic in order to ensure that the tray parts 31, 32 are mobile with respect to each other. Alternatively, the tip of the bearing device registration 50 can be supported in the recess 52 such as to be rotatable through a limited range of angles and such as to be tiltable. An adjustable screw having a counter-thread can be used as an alternative to the bearing device registration 50 in the embodiment according to FIG. 3 as well.

The bed 34 of the first tray part 31 and the bed 40 of the second tray part 32 are filled with an impression material 56 that is used to take an impression of the toothless or partly toothed jaw.

If both markings 38, 48 are imaged intra-orally using a method according to the invention, the position and the orientation of the tray parts 31, 32 with respect to each other can be determined. This information allows an appropriate configuration of teeth in the denture and/or dental prosthesis to be generated. The denture and/or dental prosthesis can then be generated directly using a CAD/CAM method.

Figure 3B:
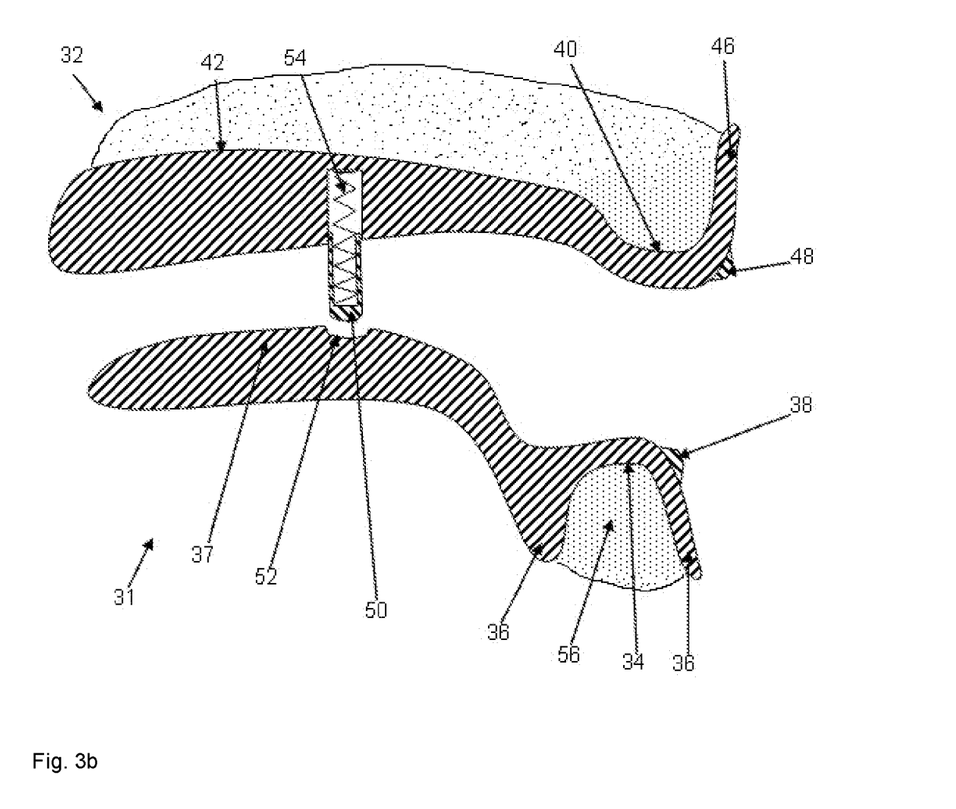

FIG. 3b corresponds to FIG. 3a. The difference being that the bed 34 of the afore-described first tray part 31 (see description of FIG. 3a) is fully filled with an impression material 56 and the bed 40 of the second tray part 32 is filled with an impression material 56 as described above. This is used to take the impression of the edentulous or partly edentulous jaw, whereby an impression of the upper jaw and upper palate is obtained with the first tray part 31.

The features of the invention disclosed in the preceding description and in the claims, figures, and exemplary embodiments, can be essential for the implementation of the various embodiments of the invention both alone and in any combination.

LIST OF REFERENCE NUMBERS 1, 31 Tray part for the lower jaw
2, 32 Tray part for the upper jaw
3, 13 Rigid connecting element
4, 10, 34, 40 Bed for accommodation of the impression material
6, 16, 36, 46 Wall of the bed
7, 37 Tongue shield
8, 18, 38, 48 Marking
12, 42 Palate plate
14 Lip shield
15 Lip shield bracketing
20 Elastic bearing device registration/Spring-loaded bearing device registration/lockable screw
22, 52 Recess for bearing device registration/screw
50 Spring-loaded bearing device registration
52 Recess for bearing device registration
54 Spring
56 Impression material

The invention claimed is:

1. A method for taking an impression of at least partial regions of an upper and lower jaw of a patient for producing a dental prosthesis, said method comprising the steps of:

A) generating an impression of at least partial regions of the upper jaw and lower jaw of the patient using an at least two-part tray in an oral cavity of the patient, whereby the tray is inserted into the oral cavity of the patient for this purpose;

wherein the at least two-part tray comprises at least one tray part for the upper jaw and at least one tray part for the lower jaw, whereby the tray parts are placed at a distance from each other by means of a screw or a pin, and are attachable at an adjustable distance from each other, wherein the pin, which comprises a mobile pestle that is supported against one of the tray parts as in a bearing in spring-loaded manner, or the screw is arranged on one of the tray parts, whereby the other tray part comprises a recess for accommodation of a tip of the screw or a tip of the pestle, whereby the recess comprises a matching counter-thread for the screw or the recess is a negative fit for the tip of the pestle, whereby the tip of the pestle is arranged appropriately mobile in the recess such that it can be inclined towards all sides, wherein at least one marking is arranged on a surface of each tray part and the markings are arranged on an edge of the tray parts such that the markings of adjacent tray parts that are inserted into the oral cavity of the patient are situated as close to each other such that the markings can be imaged on just one image of a recording device in the oral cavity of the patient, B) fixing the at least two tray parts to each other or against each other in the oral cavity of the patient;

C) thereafter determining the position and orientation of the at least two tray parts with respect to each other in the oral cavity of the patient;

wherein the position and orientation of the tray parts with respect to each other are determined by means of the at least one marking on each of the tray parts arranged on a labial surface of the tray parts, wherein the at least one marking is a three-dimensional contoured marking that permits tilting of the marking to be recognized and measured; wherein the position and orientation of the markings of the tray parts are determined with respect to each other and data obtained regarding the position and orientation of the markings are used to determine the position and orientation of the tray parts with respect to each other; and wherein the position and orientation of the tray parts are determined with respect to each other by intra-orally imaging or scanning with an optical method the labial surfaces of the tray parts, at least regions thereof, whereby at least two markings of at least two different tray parts are imaged or scanned concurrently, and D) thereafter taking the tray parts out of the oral cavity of the patient.

2. Method according to claim 1, which further comprises determining the position and orientation of the tray parts with respect to each other by recording, digitizing and analyzing regions of the tray parts, which regions optionally comprise the markings, in a computer-based manner by means of a stereo image or at least two images taken from different perspectives.

3. Method according to claim 1, which further comprises detaching the at least two tray parts from each other before removing from the oral cavity of the patient and after determining the position and orientation of the at least two tray parts with respect to each other, and removing the tray parts from the oral cavity separately.

4. Method according to claim 1, which further comprises providing a lip shield as at least a third tray part and optionally attaching the lip shield to the tray part for the upper jaw, whereby the lip shield optionally has at least one marking that is used to determine the position and orientation of the lip shield with respect to the tray part for the upper jaw and/or that the lip shield has a surface provided on it on which can be written and which serves to have aesthetic features drawn on it and which has at least one aesthetic feature drawn on it.

5. Method according to claim 1, which further comprises storing the position and orientation of the at least two tray parts with respect to each other in a computer and using them to calculate a virtual model of the dental prosthesis to be produced, and optionally to calculate the orientation and size of the dental prosthesis of a denture for the upper jaw and/or a denture for the lower jaw of the patient.

6. Method according to claim 5, which further comprises producing the dental prosthesis by means of a CAD/CAM method, whereby the position and orientation of the at least two tray parts with respect to each other are utilised in the generation of a virtual CAD model.

7. Method according to claim 1, which further comprises using an impression of the upper jaw and/or lower jaw of the patient taken with the tray to generate a data set by reading a three-dimensional surface structure of the impression of the upper jaw and/or lower jaw of the patient, and optionally using the data set to generate the virtual CAD model of the dental prosthesis, optionally a denture, which is used to produce a real dental prosthesis, optionally a real denture.

8. Method according to claim 1, which further comprises attaching a rigid connecting element with multiple markings, optionally an irregular raster or an irregular grid, to the at least two tray parts and using the connecting element to determine the position and orientation of the at least two tray parts with respect to each other.

9. A method for taking an impression of at least partial regions of an upper and lower jaw of a patient for producing a dental prosthesis, said method comprising the steps of:

A) generating an impression of at least partial regions of the upper jaw and lower jaw of the patient using an at least two-part tray in an oral cavity of the patient, whereby the tray is inserted into the oral cavity of the patient for this purpose;

B) fixing the at least two tray parts to each other or against each other in the oral cavity of the patient;

C) thereafter determining the position and orientation of the at least two tray parts with respect to each other in the oral cavity of the patient;

wherein the position and orientation of the tray parts with respect to each other are determined by means of at least one marking on each of the tray parts arranged on a labial surface of the tray, wherein the at least one marking is a three-dimensional contoured marking that is elevated with respect to and projects from said surface of the tray that permits tilting of the marking to be recognized and measured; and wherein the position and orientation of the markings of the tray parts are determined with respect to each other by intra-oral imaging or scanning with an optical method the labial surfaces of the tray parts, at least regions thereof, whereby at least two markings of at least two different tray parts are imaged or scanned concurrently and data obtained regarding the position and orientation of the markings are used to determine the position and orientation of the tray parts with respect to each other, and D) thereafter taking the tray parts out of the oral cavity of the patient.

* * * * *